United States Patent [19]
Burns et al.

[11] Patent Number: 5,635,168
[45] Date of Patent: Jun. 3, 1997

[54] COMPOSITION FOR TREATING HAIR

[75] Inventors: Michael S. Burns, Doylestown, Pa.;
Herbert E. Edelstein, Stratford, Conn.

[73] Assignee: Business Resources Group, Inc., Newtown, Pa.

[21] Appl. No.: 310,270

[22] Filed: Sep. 21, 1994

[51] Int. Cl.$^6$ .................................. A61K 7/06
[52] U.S. Cl. ............... 424/70.4; 424/70.5; 424/70.51; 424/706
[58] Field of Search ................ 424/706.1, 70.4, 424/70.5, 70.51

[56] References Cited

U.S. PATENT DOCUMENTS

| | | | |
|---|---|---|---|
| 2,540,494 | 2/1951 | Schwarz | 132/205 |
| 2,719,104 | 9/1955 | Westerberg | 8/432 |
| 3,215,605 | 11/1965 | Soloway | 8/425 |
| 3,266,994 | 8/1966 | Reiss et al. | 8/127.51 |
| 3,396,736 | 8/1968 | Shansky | 132/208 |
| 3,399,682 | 9/1968 | Isaji et al. | 132/204 |
| 3,399,683 | 9/1968 | Forbriger et al. | 132/205 |
| 3,865,930 | 2/1975 | Abegg et al. | 424/70.4 |
| 3,912,446 | 10/1975 | Zviak et al. | 8/425 |
| 4,149,848 | 4/1979 | Bugaunt | 8/410 |
| 4,173,453 | 11/1979 | Shiah | 8/10.1 |
| 4,186,188 | 1/1980 | Gumprecht | 424/70.14 |
| 4,494,557 | 1/1985 | Nagel | 132/207 |
| 4,630,621 | 12/1986 | Pontani | 132/204 |
| 4,658,839 | 4/1987 | Dallal et al. | 132/203 |
| 4,776,856 | 10/1988 | Tennigkeit et al. | 8/406 |
| 4,793,992 | 12/1988 | Mathews et al. | 424/538 |
| 4,840,791 | 6/1989 | Mathews et al. | 424/70.5 |
| 4,906,461 | 3/1990 | Chambers | 424/74 |
| 4,947,878 | 8/1990 | Crews et al. | 132/203 |
| 4,992,077 | 2/1991 | Tennigkeit et al. | 8/406 |
| 5,006,127 | 4/1991 | Tennigkeit et al. | 8/406 |
| 5,015,470 | 5/1991 | Gibson | 514/2 |
| 5,034,226 | 7/1991 | Beck | 424/195.1 |
| 5,051,252 | 9/1991 | Schultz et al. | 424/70.4 |
| 5,094,662 | 3/1992 | Schultz et al. | 8/406 |
| 5,101,841 | 4/1992 | Crews et al. | 132/203 |
| 5,139,772 | 8/1992 | Morita et al. | 424/70.4 |
| 5,161,553 | 11/1992 | Cohen et al. | 132/205 |
| 5,188,639 | 2/1993 | Schultz et al. | 8/405 |
| 5,241,973 | 9/1993 | Sake et al. | 132/205 |
| 5,338,540 | 8/1994 | Lee et al. | 424/71 |
| 5,340,367 | 8/1994 | Schultz et al. | 8/432 |

FOREIGN PATENT DOCUMENTS

| | | |
|---|---|---|
| 0260716 | 3/1988 | European Pat. Off. |
| 0328816 | 8/1989 | European Pat. Off. |
| 0443356 | 7/1993 | European Pat. Off. |
| 4211451 | 10/1993 | Germany . |
| 4331136 | 8/1994 | Germany . |
| 96336-1978 | 8/1978 | Japan . |
| 60/100512 | 6/1985 | Japan . |
| 2153865 | 8/1985 | United Kingdom . |

OTHER PUBLICATIONS

Redken advertisement, "CAT™Protein Network System," 1 page (1990).
M.S. Balsam (editor), *Cosmetics Science And Technology*, vol. 2, pp. 224–229 (second edition 1972).
W.A. Poucher (revised by G.M. Howard), *Perfumes, Cosmetics and Soaps*, vol. 3, pp. 93–105 (eighth edition 1974).
Croda Inc., Product List, pp. 1, 7, 8 (Apr. 1990).
Croda Inc., Hydrotriticum 2000 Data Sheet, 2 pages (May 2, 1994).
Croda Inc., Hydrosoy 2000/SF Data Sheet, 2 pages (Jul. 19, 1984).
Croda Inc., Croquat WKP Data Sheet, 5 pages (1988).
Croda Inc., Crotein WKP Data Sheet, 4 pages.
Prodesign International, "Pro–Ionic Quench —Perm Rinse Eliminator," 3 pages (1993/1994).
*Hawley's Condensed Chemical Dictionary*, entries for "cysteine," cystine, and keratin (11th ed. 1987).
*Merck Index*, Windholz et al., "Cystine" p. 400, abstract No 2776 (1983).

Primary Examiner—Kevin E. Weddington
Attorney, Agent, or Firm—Bryan Cave LLP

[57] ABSTRACT

A composition and a method for treating hair are disclosed. The composition improves properties such as the hand (feel), curl retention, color receptivity, color retention, shine, and strength of the hair and the compositions can be used to prevent or repair damage to hair caused by hair treating processes (e.g., hair waving and coloring). The composition is useful in a rinse-free waving process, that is, a permanent waving process in which the intermediate rinse between the reducing step (the waving step) and the oxidizing step (the neutralization step) is omitted. The composition is also useful in a coloring process and in a one-day combined rinse-free waving and coloring process. The composition contains (1) an alkaline earth metal (e.g., magnesium or calcium), zinc, or aluminum, preferably in the form of a water-soluble salt (e.g., magnesium sulfate), (2) a low molecular weight sulfur-containing material that can form disulfide bonds involving the keratin of the hair (e.g., cystine-containing materials such as polypeptides or other proteinaceous materials) and (3) optionally an acid, which can be a carboxylic acid (e.g., a hydroxycarboxylic acid such as citric acid) or other organic acid (e.g., acetic acid) or mineral acid. The pH of the composition is less than 7, usually ranges from 2 to 6.5, and is preferably about 2 to 3.5 when used in the rinse-free waving process.

69 Claims, No Drawings

COMPOSITION FOR TREATING HAIR

BACKGROUND OF THE INVENTION

The invention concerns hair treating compositions and their methods of use. More specifically, the invention concerns compositions that when applied to hair improve properties such as its hand (feel), curl retention, color receptivity, color stability, color retention, shine, and strength and that can be used to prevent or repair damage to hair caused by hair treating processes (e.g., hair waving and coloring).

Hair treating compositions and methods for treating hair have been used for many years. Compositions used include coating compositions to hold hair in a particular manner and compositions to improve hair strength, shine, color, arrangement, or other properties or to prevent or repair damage to hair. Current popular hair treatments include permanent waving and hair coloring, both of which involve chemical treatments that tend to injure hair.

There are numerous methods and compositions for permanent waving, which involves arranging the hair in the desired configuration and then treating the hair to semi-permanently retain the arrangement. The initial step is a waving step in which the hair is "relaxed" by breaking the disulfide bonds in the keratin of the hair using a reducing agent. Compositions used to break those bonds include solutions of thioglycolic acid (at pH 8.5-9.5 if an alkaline wave or pH 6.5-6.95 if an acid wave) or a sulfite/bisulfite solution (at pH 5.5-8.5) containing alkalis such as alkali metal compounds, ammonium hydroxide, or amines (e.g., monoethanolamine) to provide the alkaline pH. After breaking the keratin's disulfide bonds, the hair is fixed in the desired arrangement using an oxidizing agent (e.g., hydrogen peroxide or sodium bromate) to reestablish disulfide bonds in the keratin.

The reduction within the hair fiber is of the amino acid cystine, which contains a centrally located disulfide bond. When this bond in a cystine molecule is cleaved using the reducing solution (usually called the "waving solution"), the cystine molecule forms two molecules of the amino acid cysteine, each having a terminal sulfhydryl group resulting from the disulfide cleavage.

If the hair is to be curled, the hair is typically rolled onto rods of various sizes, contacted with the reducing (or waving) solution, and permitted to remain in contact with the solution until the required amount of reduction has occurred. Typically, the at-least-partially-spent reducing solution or lotion is thoroughly rinsed from the hair, the hair is towel dried, and the neutralizer (oxidizing composition) is applied. The neutralizer reoxidizes the sulfhydryl groups to disulfide groups to fix the hair in the new arrangement. If curls are required, the hair is neutralized while still on the rods. Hair may also be straightened, i.e., the natural curl removed from the hair, in which case the hair is combed while in contact with the reducing solution and then combed while the neutralizer or oxidizing solution is applied. In either case (curling or straightening), the procedure is completed by rinsing the neutralizer (oxidizer) from the hair. It is usually recommended that hair not be shampooed for at least 24 hours after the permanent waving procedure to provide the tightest curl or straightest hair, as the case may be, because even after removal of the oxidizing solution from the surface of the hair, reaction within the hair (i.e., reformation of disulfide bonds) continues.

Many attempts have been made to provide waving and other treating compositions that prevent some or all of the damage to the hair before it occurs or that repair the damage after it has occurred. See, e.g., U.S. Pat. Nos. 3,266,994, 4,186,188, 4,494,557, 4,658,839, 4,793,992, 4,906,461, 5,015,470, and 5,051,252, U.K. Patent Application No. 2,153,865, and EPO Patent No. 443,356. (All of those documents as well as all others referenced and/or discussed herein are incorporated herein in their entireties for all purposes.)

Some hair treating compositions include salts (e.g., salts of polyvalent metals); see, e.g., U.S. Pat. Nos. 3,266,994 and 5,051,252 and U.K. Patent Application No. 2,153,865. Some hair treating compositions include proteins or polypeptides or amino acids (e.g., keratin, which is an important constituent of hair, nails, wool, and feathers, or low molecular weight protein fragments such as hydrolyzed protein, or amino acids such as cystine and cysteine, the first of which is a constituent of the keratin in the hair and the second of which results from the cleavage of cystine); see, e.g., U.S. Pat. Nos. 4,186,188, 4,494,557, 4,658,839, 4,793,992, and EPO 443,356. Some hair treating compositions use proteinaceous material and salt. See, e.g., U.S. Pat. No. 4,494,557, which concerns an aqueous hair conditioning composition for permanent waving that contains (a) 15.7 to 34.8% of a reconstructor solution, the preferred reconstructor solution containing hydrolyzed animal protein and keratin having 3.2% cystine, and (b) 24.1 to 41.6% magnesium sulfate. (Commercial KERAPHIX, the preferred reconstructor solution used in U.S. Pat. No. 4,494,557, is said to contain numerous ingredients, including keratin amino acids, glycerine, mineral oil, safflower oil, zinc chloride, magnesium citrate, and manganese citrate.) Some hair treating compositions include acids (e.g., mineral acids or carboxylic acids such as citric acid); see, e.g., U.S. Pat. Nos. 3,266,944, 4,793,992, 4,906,461, and 5,015,470. Some hair treating compositions use all three types of materials, namely, salts of polyvalent metals, proteins or polypeptides or amino acids, and mineral or carboxylic acids; see, e.g., U.S. Pat. Nos. 4,793,992 and 4,906,461.

Proteins said to be useful in hair treatment by their purveyor, Croda Inc., include HYDROTRITICUM 2000 (hydrolyzed whole wheat protein, which has an average molecular weight of 3,000, is available as a 20% solution, contains 1.8% cystine, contains 1.3% methionine, and is said typically to be used at a 1-5% level) and other HYDROTRITICUM preparations, HYDROSOY 2000/SF (hydrolyzed soy protein solution, which has an average molecular weight of about 4,000, is available as a 20% solution, contains 1.0% cystine, contains 1.3% methionine, and is said typically to be used at a 0.2-3% level), KERASOL (a soluble keratin preparation, which has an average molecular weight of about 125,000), CROQUAT WKP (cocodimonium hydrolyzed animal keratin, which has an average molecular weight of about 1,000, is available as a 30% solution, contains about 10.2% cystine and no methionine, and is said typically to be used at a 0.25-2% level) and other CROQUAT preparations, CROTEIN WKP (hydrolyzed wool-based protein, which has an average molecular weight of about 600, is available as a 22% solution, contains about 10.2% cystine and no methionine, and is said typically to be used at a 0.2-3% level) and other CROTEIN preparations, and CROSILKQUAT (cocodimonium silk amino acids, which has an average molecular weight of 320, is available as a 30% solution, contains 0.2% methionine, and contains 0.1% cystine). The presence of cystine in some of these materials is said by Croda to be particularly desirable because, among other reasons, the cystine can permanently bind to the hair under certain conditions and can minimize the loss of cystine from the keratin of the hair during waving.

The hydrolyzed proteins used in the formulation referenced in column 5, lines 3–22, of U.S. Pat. No. 4,793,992 are CROTEIN SPC (hydrolyzed collagen, which has an average molecular weight of 10,000, is available as a powder with an activity of 93%, contains 0.7 to 0.9% methionine, and contains no more than 0.9% cystine), CROSILK LIQUID (mixture of amino acids derived from hydrolyzed silk protein, which has an average molecular weight of 92, contains 0.2% methionine, and contains about 0.1% cystine), and AMINO GLUTEN MG (mixture of amino acids derived from maize gluten protein, which contains little or no methionine and no cystine). Those three materials are all marketed by Croda Inc. and the formulation of the patent contains 2% of each of them, for a total of 6% of the formulation. In addition, the referenced formulation of U.S. Pat. No. 4,793,992 contains 0.1% of the hydrolyzed protein that is described in U.S. Pat. No. 4,186,188, 2.5% magnesium sulfate, and 1% citric acid and it has a pH of about 5.

A hair conditioner marketed by Redkin Laboratories, Inc. under the name CAT is believed to have a pH of about 6.6 and to contain about 0.4% magnesium sulfate, more than 0.4% soy protein, less than 0.4% CROQUAT WKP, and optionally citric acid, with a total of about 3% solids.

As noted above, the typical permanent waving process requires a rinsing step between the application of the reducing solution and the application of the oxidizing (neutralizing) solution. This intermediate rinse is widely thought to be needed to remove as much of the reducing solution as possible from the hair because the pH of the reducing solution is usually higher than that of the oxidizing solution and if left on the hair in any significant amount, the reducing solution would react with a significant amount of the oxidizing (neutralizing) solution and reduce the latter's effectiveness, especially in the hair fibers into which the oxidizing solution had poorly penetrated. The failure to reform enough disulfide bonds, e.g., if the neutralizer were not sufficiently effective (as would be the case if the reducing solution left on the hair significantly reduced the efficacy of the neutralizer), is highly undesirable because the resulting hair will have poor curl and tend to be straw-like, brittle, feel rough, etc. Hence, the generally recognized need for the intermediate rinse.

On the other hand, it would be desirable to eliminate the intermediate rinse, that is, to use a "rinse-free waving process," because the rinsing step: causes loss of keratin, amino acids, and color from the hair fiber; causes physical damage to the cuticle and cortex of the hair because of the pressurized water jets typically used in hair salons during rinsing; utilizes approximately nine gallons of water with every permanent; is time-consuming, thereby reducing the number of permanent wave customers a hair salon can service per day; and causes swelling of the fiber over and above that caused by the waving lotion. The damage caused by excessive swelling is generally irreversible. (As used herein, the term "rinse-free waving process" will be used to refer to all types of waving processes, including curling and straightening processes, in which there is no intermediate rinse, that is, there is no rinse between application of the waving (reducing) solution and application of the neutralization (oxidizing) solution.)

U.K. Patent Application 2,153,865 concerns a waving process. Hair is treated with reducing solution to achieve substantially maximum cystine cleavage, blotted to remove the reactive reducing solution, contacted with a so-called protein flow solution, arranged in the desired configuration, rinsed, and contacted with an oxidizing agent to reestablish the cystine bonds. The protein flow solution is an aqueous solution containing a polyvalent metal having acceptable toxicity (for example, a magnesium or calcium salt, e.g., magnesium sulfate) in a concentration of about 1 to 10% by weight of the solution and/or a water-soluble hydroxyorganic compound containing one or more hydroxyl groups and up to about 4 carbon atoms, namely, an alcohol or polyol (for example, ethanol). The pH is desirably 2 to 10, preferably about 6 to 7, and may be adjusted using alkaline compounds such as alkaline amino acids (cystine and cysteine peptides, proteins, and amino acids are acidic and not alkaline).

A recently marketed product, PRO-IONIC QUENCH™ from Pro-Design International, is said to be useful in a rinse-free waving process in which two different solutions are applied to the hair after waving and blotting and before neutralization. The first solution is believed to have a pH of about 8.3, to contain a bicarbonate salt, and to have only about 5 parts per million of magnesium. The second solution is believed to have a pH of about 2.4 and to contain about 4.5% magnesium sulfate, some citric acid or sodium citrate, and some HYDROTRITICUM (which contains about 1.8% cystine and about 1.5% methionine). The product is said to improve hair strength, color retention, etc.

It is known that the best time to place hair strengthening agents into the cortex of the hair is after the waving solution has swollen the fiber, which swelling opens the cortex, and before the neutralizer deswells or shrinks the fiber. It is also known that it is desirable to protect the cuticle and cortex of the hair from the damaging effects of the neutralizer solution.

Separate and apart from waving processes, it is also desirable to impart color receptivity, color stability, color retention, good hand, softness, manageability, curl strength and retention, etc. to hair that has been or is being colored either in a coloring process or in a combined waving and coloring process. It is also desirable to impart such properties to hair that may have been damaged by waving, coloring, or other processes and/or by environmental factors (e.g., excessive sunlight).

Despite the substantial work done over the years, the need remains for a hair treating composition that when applied to hair can improve properties such as its hand (feel), curl retention, color retention, shine, strength, and the other properties mentioned herein and that can be used to prevent or repair damage to hair caused by hair treating processes (e.g., hair waving and coloring) and environmental factors.

SUMMARY OF THE INVENTION

Compositions and methods that meet those needs, overcome those problems, and provide additional benefits have now been discovered. Broadly speaking, the composition of this invention is an aqueous composition useful for treating hair comprising:

(a) at least 1% by weight total of one or more polyvalent metal compounds;

(b) a sulfur-containing material that has an average molecular weight of 10,000 or less, that can form disulfide bonds involving the keratin of the hair, and whose sulfur content is at least about 1% by weight; and (c) optionally, an acid;

the pH of the composition being less than 10.

In another aspect, the composition of this invention is an aqueous composition useful for treating hair comprising:

(a) at least 1% by weight of a polyvalent metal compound selected from the group consisting of alkaline earth metal compounds, zinc compounds, and aluminum compounds;

(b) a cystine-containing proteinaceous material that has an average molecular weight of 5,000 or less, that can form disulfide bonds involving the keratin of the hair, and whose cystine content is at least about 3.5% by weight; and (c) optionally, an acid selected from the group consisting of carboxylic acids and mineral acids;

the pH of the composition being less than 10.

In another aspect, the composition of this invention is an aqueous composition useful for treating hair comprising:

(a) at least 2% by weight of a polyvalent metal compound selected from the group consisting of alkaline earth metal compounds, zinc compounds, and aluminum compounds;

(b) a cystine-containing proteinaceous material that has an average molecular weight of 2,000 or less, that can form disulfide bonds involving the keratin of the hair, and whose cystine content is at least about 3.5% by weight; and (c) an acid selected from the group consisting of carboxylic acids and mineral acids;

the pH of the composition being less than 10.

In still another aspect, the composition of this invention is an aqueous composition useful for treating hair comprising:

(a) 4 to 15% by weight of a polyvalent metal compound selected from the group consisting of alkaline earth metal compounds, zinc compounds, and aluminum compounds;

(b) 0.01 to 5% by weight of a cystine-containing proteinaceous material that has an average molecular weight of 1,000 or less, that can form disulfide bonds involving the keratin of the hair, and whose cystine content is at least about 3.5% by weight; and (c) 0.001 to 5% by weight of an acid selected from the group consisting of carboxylic acids and mineral acids;

the pH of the composition being less than 10.

In another aspect, the present invention concerns a rinse-free waving process for hair comprising the steps:

(a) contacting the hair with a reducing composition until the desired amount of reduction of the disulfide bonds in the hair has occurred;

(b) optionally removing excess reducing composition from the hair without rinsing;

(c) contacting the hair with a composition of this invention without any rinsing of the hair between this step (c) and step (a), wherein the pH of the composition used in this step (c) prior to contacting with the hair is from about 2 to about 3.5;

(d) thereafter optionally removing from the hair any excess of the composition contacted with the hair in step (c); and (e) contacting the hair that has been contacted with the composition in step (c) with an oxidizing composition to reform disulfide bonds in the hair without any rinsing of the hair between this step (e) and step (c).

In another aspect, the present invention concerns a rinse-free waving process for hair comprising the steps:

(a) contacting the hair with a reducing composition until the desired amount of reduction of the disulfide bonds in the hair has occurred;

(b) optionally removing excess reducing composition from the hair without rinsing;

(c) contacting the hair with a mixture comprising (i) a composition of this invention and (ii) an oxidizing composition to reform disulfide bonds in the hair, without any rinsing of the hair between this step (c) and step (a), the pH of the mixture prior to contacting the hair being 4 or less.

In another aspect, the present invention concerns a coloring process for hair comprising the steps:

(a) contacting the hair with a composition of this invention;

(b) thereafter optionally drying the hair; and (c) thereafter contacting the hair with a coloring composition.

In another aspect, the present invention concerns a combined rinse-free waving and coloring process for hair, all the steps of which can be performed within a period of twenty-four hours, comprising the steps:

(a) processing the hair according to a rinse-free waving process of this invention;

(b) thereafter optionally drying the hair; and (c) thereafter contacting the hair with a coloring composition.

In another aspect, the present invention concerns a process for conditioning the hair, optionally prior to waving the hair, said conditioning process comprising the steps:

(a) contacting the hair with a composition of this invention; and (b) thereafter optionally waving the hair.

In preferred embodiments the polyvalent metal compound is magnesium sulfate and is present in an amount of about 6 to 9% by weight, the acid is citric acid and is present in an amount of from 0.01 to 3% by weight, and the proteinaceous material has an average molecular weight of about 1,000 or less, contains at least 8% cystine, and is present in an amount of from 0.2 to 3% by weight.

With respect to the rinse-free waving process, if the neutralizer (oxidizer) is strong enough (e.g., if hydrogen peroxide is used, a peroxide concentration of 4% or higher), in some cases it may be possible to omit the polyvalent metal(s), although it may be that not all the benefits of this invention will be realized. Thus, in another aspect the present invention concerns a rinse-free waving process for hair comprising the steps:

(a) contacting the hair with a reducing composition until the desired amount of reduction of the disulfide bonds in the hair has occurred;

(b) optionally removing excess reducing composition from the hair without rinsing;

(c) contacting the hair with a composition comprising (i) optionally, one or more polyvalent metal compounds; (ii) a sulfur-containing material that has an average molecular weight of 10,000 or less, that can form disulfide bonds involving the keratin of the hair, and whose sulfur content is at least about 1% by weight; and (iii) optionally, an acid; without any rinsing of the hair between this step (c) and step (a), wherein the pH of the composition used in this step (c) prior to contacting with the hair is from about 2 to about 3.5;

(d) thereafter optionally removing from the hair any excess of the composition contacted with the hair in step (c); and (e) contacting the hair that has been contacted with the composition in step (c) with an oxidizing composition to reform disulfide bonds in the hair without any rinsing of the hair between this step (e) and step (c).

In yet another aspect, the present invention also concerns a rinse-free waving process for hair comprising the steps:

(a) contacting the hair with a reducing composition until the desired amount of reduction of the disulfide bonds in the hair has occurred;

(b) optionally removing excess reducing composition from the hair without rinsing;

(c) contacting the hair with a mixture comprising (i) a composition comprising (A) optionally, one or more polyvalent metal compounds; (B) a sulfur-containing material that has an average molecular weight of 10,000 or less, that can form disulfide bonds involving the keratin of the hair, and whose sulfur content is at least about 1% by weight; and (C) optionally, an acid; and (ii) an oxidizing composition to reform disulfide bonds in the hair, without any rinsing of the hair between this step (c) and step (a), the pH of the mixture prior to contacting the hair being 4 or less.

This invention provides numerous benefits. With respect to a rinse-free waving process, use of a composition of this invention between application of the reducing mixture and application of the oxidizing mixture allows one to eliminate the intermediate rinsing step with its attendant disadvantages, including those set forth above. The rinse-free waving process of this invention infuses strengthening agents into the hair fiber, does not impede neutralization and rebonding, and yields greater curl retention, and softer, stronger, shinier hair.

With respect to hair coloring, use of a composition of this invention in combination with a color process reduces the damage to the hair that would otherwise be caused by the color process, improves the shine and gloss of the colored hair, results in more even hair color, and results in better color penetration of the hair, thereby increasing color receptivity, color stability, and color retention. For example, use of a composition of this invention in conjunction with a color process for "high lift" blonde hair reduces the time and work required for color correction to bring the hair to the correct level for color deposit (it typically requires 20 minutes of processing time for an experienced operator to even the hair porosity and bring the hair into a color range that will ensure correct color deposit). Without such pre-processing (color corrective work), the resulting color will not be correct. Use of the present composition eliminates that time and work and results in a color that is deep and rich and that has the same tonal values that the color manufacturer intended. Furthermore, an inexperienced individual can do this work in a fail-safe manner, which is not the case for traditional color correction.

With respect to a combined rinse-free waving and coloring process, the combined process can be carried out in less than a day and in a single session. That improves salon efficiency by reducing scheduling problems and the risk of cancelled appointments, thereby improving salon profitability. The beauty salon patron whose hair is being treated using such a combined process saves time (travel, scheduling, and intermediate styling time) and money because there is no need to wait a week or so between waving and coloring as is typically the case with conventional waving and coloring. Furthermore, conventional waving processes usually cause the color of previously colored hair to fade. Thus, without this invention, the patron must wait a week or so after waving until the faded color can be restored to the desired color. The patron's hair will also be healthier using the combined process of this invention because the color developer strength can be reduced. Even with that reduction, color penetration will be increased by the rinse-free step in the combined process of this invention.

With respect to hair conditioning (including the conditioning imparted by a pre-wrap process prior to a waving process), use of a composition of the present invention to condition hair improves hair properties as compared to conditioning with conventional compositions. For example, a pre-wrap step (prior to waving) using a composition of the present invention and then waving results in improved curl strength and shine and reduced hair frizziness as compared to a conventional pre-wrap followed by waving.

Regardless of in which particular process the composition of this invention is used, hair contacted with the composition has a more lustrous appearance, a softer hand, is stronger, and is more elastic than hair which has not been contacted with the composition.

DETAILED DESCRIPTION OF THE INVENTION

The composition of this invention comprises at least one polyvalent metal compound, a sulfur-containing material, and optionally an acid.

The one or more polyvalent metal compounds are preferably water-soluble salts of the alkaline earth metals, zinc, and aluminum. By "polyvalent" is meant a valence of more than one. By "alkaline earth metal" is meant a metal in Group IIA of the Periodic Table, which Group includes magnesium and calcium. The heavier metals tend to impart color to the hair and are therefore generally less desirable to use although in specific instances they may be useful. Additionally, some metals, including some of the alkaline earth metals, are less desirable for use in the present invention because of their toxicity, cost, or low solubility. In a process of this invention in which a peroxide solution is applied to the hair after or with a composition of this invention (e.g., in a rinse-free waving process using a peroxide neutralizer), some heavier metals may decompose the peroxide and are therefore not preferred. Thus, preferably the polyvalent metal compounds are sufficiently water-soluble, are non-toxic, are not too expensive, do not impart any undesired color to the hair, and do not significantly interfere with any peroxide composition used. The preferred metals are calcium, magnesium, zinc, and aluminum; however, any polyvalent metal compound may be used provided that the advantages of this invention can be achieved.

Preferably the composition contains at least one water-soluble salt of a metal selected from the group consisting of magnesium, calcium, zinc, and aluminum, of which magnesium is most preferred. Water-soluble salts such as calcium chloride, calcium acetate, magnesium chloride, magnesium sulfate, zinc chloride, zinc sulfate, and aluminum sulfate can be used, of which magnesium sulfate is most preferred. Magnesium sulfate may be used as such or in its common hydrated form, namely, Epsom salt, which has a formula of $MgSO_4 \cdot 7H_2O$.

The composition typically contains at least 1% by weight (total) of the one or more polyvalent metal compounds, usually at least 2% by weight (total) of the one or more polyvalent metal compounds, more usually from about 3 to about 20%, desirably from about 4 to about 15%, more desirably from about 5 to about 12.5%, preferably from about 6 to about 9%, more preferably from about 7 to 8%, and most preferably about 7.5% by weight. The reference to the weight or concentration of the one or more polyvalent metal compounds refers to the compounds per se and not, for example, to any related water of hydration. Thus, when using Epsom salt to provide magnesium sulfate, the water of hydration should be ignored in the calculation. For example, if 100 weight units of magnesium sulfate are needed to prepare a composition of this invention, either 100 weight units of $MgSO_4$ per se or about 204 weight units of $MgSO_4 \cdot 7H_2O$ may be used ($MgSO_4$ accounts for about 49% of the weight of $MgSO_4 \cdot 7H_2O$).

If the concentration of the polyvalent metal compound is too low, the composition does not show sufficient effectiveness in improving the condition of the hair. When the concentration of the polyvalent metal compound is above about 20% by weight of the composition, the hand (feel) of the hair may become hard and stiff.

The sulfur-containing material has an average molecular weight of 10,000 or less, can form disulfide bonds involving the keratin of the hair, and has a sulfur content of at least about 1% by weight. By "average molecular weight" is meant the number average molecular weight of the sulfur-containing material per se and not including additives (e.g., stabilizers, emulsifiers) or carriers (for example, solvents or vehicles, such as water or alcohols) that may be present in the mixture containing the sulfur-containing material. Any sulfur-containing material may be used provided that it meets those requirements and that in combination with the other ingredients the advantages of this invention are achieved. The preferred sulfur-containing materials are proteinaceous materials and particularly cystine-containing proteinaceous materials; however, it is believed that other compounds, such as mercaptoethanesulfonic acid and its salts, may be useful as the sulfur-containing material in this invention.

The term "sulfur-containing material" does not include additives (e.g., stabilizers, emulsifiers) or carriers (for example, solvents or vehicles, such as water or alcohols) that may be present in the mixture containing the sulfur-containing material. Thus, for example, if the composition containing the sulfur-containing material is a commercially available proteinaceous substance normally available in a 30% aqueous solution, the "sulfur-containing material" would not include the 70% water and the concentration of sulfur in the sulfur-containing material would be calculated based on the contained water-free sulfur-containing material rather than on the whole commercially available aqueous composition. The term "sulfur-containing material" should be understood to include not just one but also the total of two or more separate sulfur-containing materials.

The sulfur content of the sulfur-containing material refers to the weight percent sulfur in the sulfur-containing material per se and not including additives (e.g., stabilizers, emulsifiers) or carriers (for example, solvents or vehicles, such as water or alcohols) that may be present in the mixture containing the sulfur-containing material. The sulfur content of the sulfur-containing material will be at least about 1%, typically at least about 1.1%, more typically at least about 1.2%, usually at least about 1.3%, more usually at least about 1.4%, desirably at least about 1.5%, more desirably at least about 2%, most desirably at least about 2.5%, preferably at least about 3%, more preferably at least about 3.5%, and most preferably at least about 4%.

The average molecular weight of the sulfur-containing material is desirably 5,000 or less, preferably 2,000 or less, and more preferably 1,000 or less. The average molecular weight may be in the range of 300 to 2,000 and more preferably in the range of 400 to 1,000.

It is believed that molecules of a molecular weight of about 2,000 or less can enter the hair significantly more rapidly and to a greater extent than molecules having a molecular weight of more than about 2,000. Thus, if the sulfur-containing material has an average molecular weight of greater than about 2,000, it is preferred that the sulfur-containing material contain a significant number of molecules having a molecular weight of about 2,000 or less so that some portion of the overall sulfur-containing material can enter each individual hair fiber.

For reasons explained below, molecules that are too small may be less desirable for use as components of the sulfur-containing material. Thus, the average molecular weight of the sulfur-containing material will typically be at least 50, more usually at least 100, desirably at least 150, more desirably at least 200, most desirably at least 240, preferably at least 250, more preferably at least 300, and most preferably at least 400.

The concentration of sulfur-containing material in the composition of this invention is usually at least 0.001% by weight, more usually at least 0.005%, desirably at least 0.01%, more desirably at least 0.05%, preferably at least 0.10%, more preferably at least 0.15%, and most preferably at least 0.20% by weight. The concentration of sulfur-containing material in the composition of this invention will desirably be in the range of 0.01% to 5% by weight, more desirably in the range of 0.1% to 4% by weight, and most desirably in the range of 0.2% to 3% by weight. The concentration will depend to some extent on the type of sulfur-containing material used, its average molecular weight, what other ingredients are used in the composition, and their concentrations.

Desirably the sulfur-containing material is a "proteinaceous material," by which is meant a material that is or comprises one or more proteins, one or more polypeptides, one or more peptides, one or more amino acids, or mixtures thereof; however, as explained below, amino acid molecules per se are generally too small to form the desired cross-links involving the keratin of the hair and therefore it is preferred that the proteinaceous material not be only amino acids per se.

Peptides are often considered to comprise two up through several linked amino acids. (Strictly speaking, the units of the peptide are amino acid moieties, that is, molecular units derived from and substantially identical to the amino acids per se except, for example, for their terminal linked ends. When a molecule is said to contain amino acids it will be understood by those skilled in the art to contain amino acid moieties. Thus, a cystine-containing proteinaceous material may be said to contain either cystine per se or cystine moieties.) Polypeptides are often considered to comprise several up to many linked amino acid moieties. Proteins are often considered to comprise many up to hundreds, thousands, or even more linked amino acid moieties. As is apparent, there is often no clear cut dividing line between peptides and polypeptides or between polypeptides and proteins. For reasons explained herein, it is desirable that the proteinaceous material not consist entirely of molecules that are too large or too small. The term "proteinaceous material" should be understood to include not just one but also the total of two or more separate proteinaceous materials. The proteinaceous material may be derived from any source and by any method.

Preferably the sulfur-containing material is a cystine-containing proteinaceous material (the amino acid cystine contains about 26.7% by weight of sulfur). When a cystine-containing material is used, its cystine content is usually at least about 3.5% by weight, desirably at least about 6% by weight, more desirably at least about 8% by weight, and preferably at least about 10% by weight. The preferred commercially available proteinaceous materials, CROTEIN WKP and CROQUAT WKP (described above), typically contain about 10.2% cystine. The term "cystine-containing proteinaceous material" should be understood to include not just one but also the total of two or more separate cystine-containing proteinaceous materials used in the composition.

A mixture of cationic and non-ionic cystine-containing proteinaceous materials works well in the composition of this invention. If such a mixture is used as the sulfur-containing material, the weight ratio of cationic to non-ionic proteinaceous materials should be from 4/1 to 1/4 (the ratio is of active ingredient to active ingredient and does not include any carrier, for example, water, or any other additives). The two preferred cystine-containing proteinaceous materials are CROQUAT WKP, which is cocodimonium hydrolyzed animal keratin and is cationic (average molecular weight of about 1,000; sold as a 30% aqueous solution), and CROTEIN WKP, which is hydrolyzed wool-based protein and is non-ionic (average molecular weight of about 600; sold as a 22% aqueous solution). A weight ratio of 3 weight units of CROQUAT WKP solution to 4 weight units of CROTEIN WKP solution is preferred. Thus, when the solution concentrations are taken into account, the preferred weight ratio of these cationic to non-ionic materials is equal to (3×30%) divided by (4×22%) or slightly more than 1/1.

It is important that the sulfur-containing material be able to form disulfide bonds involving the keratin of the hair. As used herein, the phrase "can form disulfide bonds involving the keratin of the hair" means that the sulfur-containing material can bond to the keratin in the hair through, with, or by means of thiol moieties or disulfide bonds, can form disulfide bonds (e.g., cross-links) between different parts of the keratin of the hair (e.g., can form disulfide bonds to cross-link two cysteines in the hair and thereby form a cystine), and/or can form disulfide bonds that otherwise involve the keratin of the hair. Methionine is a sulfur-containing amino acid and is present in some proteinaceous materials that may be used in this invention; however, methionine cannot form disulfide bonds involving the keratin of the hair and is generally not useful in this invention.

Because it is desirable that the sulfur-containing material be able to form disulfide bonds involving the keratin of the hair, molecules of amino acids per se are less desirable for use as the proteinaceous material because they will generally not be large enough to bridge the molecular spacing between reactive portions of the hair (e.g., the cysteines moieties) to form desired cross-links. Accordingly, it is preferred that the proteinaceous material not be only amino acids per se; however, amino acids can be used as part of the proteinaceous material provided that the proteinaceous material comprises larger molecules (e.g., peptides, polypeptides, and proteins) that can form the desired cross-links involving the keratin of the hair. If amino acids per se are present, desirably they comprise no more than 50% by weight of the sulfur-containing or proteinaceous material, more desirably no more than 40%, most desirably no more than 30%, preferably no more than 20%, more preferably no more than 10%, and most preferably no more than 5%.

The cysteine in the hair, e.g., resulting from the cleavage of the disulfides of cystine of the hair's keratin (the cleavage occurring naturally or as a result of the use of waving solution), will be the principal part of the keratin in the hair participating in the reformation of cystine. About half of the cystine is outside the cuticle of the hair and the other half is inside the cuticle of the hair. That is why it is important that at least some of the active ingredients of the composition of this invention (that is, the at least one polyvalent metal compound, the sulfur-containing material, and the optional acid) be able to penetrate and actually do penetrate the hair so that the cysteine inside the cuticle (in addition to the cysteine outside the cuticle) can participate in formation of the disulfide bonds involving the keratin of the hair. Hence the preference that the sulfur-containing material contain a significant number of molecules having a molecular weight of about 2,000 or less regardless of the actual average molecular weight of the sulfur-containing material. The polyvalent metal compounds and the acid will almost always be small enough so that penetration of enough of each of them into the hair will not usually be a problem.

The pH of the composition of this invention will generally be 10 or less and will usually be at least 2 (a pH less than about 2 may pose safety problems) and 6.5 or less, typically 6.0 or less, desirably 5.5 or less, more desirably 5.0 or less, preferably 4.5 or less, more preferably 4.0 or less, and most preferably 3.5 or less. The specific pH of a particular composition will depend on its intended use. For example, when used in a rinse-free acid waving process, the pH of the composition will be 5.5 or less, preferably from about 3.5 to 4.0 (the composition of the invention will usually be at a sufficiently low pH to result in the hair having a pH below about 6.5 after contact with the acid waving lotion and the composition of the invention); when used in a rinse-free alkaline waving process, the pH of the composition will be 4 or less, preferably from about 2.0 to 3.5 (the composition of the invention will usually be at a sufficiently low pH to result in the hair having a pH below about 7.0 after contact with the alkaline waving lotion and the composition of the invention). When used as a conditioner, the pH of the composition will be 6.5 or less, preferably from about 3.5 to 5.5. When used in a color process, the pH of the composition will be above 3, generally 3.5 to 10, and usually from about 3.5 to 6.5. When used as a pre-wrap, the pH of the composition will be 5.5 or more, preferably from about 5.5 to 6.5. Higher or lower pH may be used in a particular case provided the benefits of this invention are still achieved.

Depending on the particular polyvalent metal compound (s) and sulfur-containing materials used, the aqueous composition of this invention containing them may have a pH below 7 and within the desired range for the intended use, in which case it will not be necessary to add a pH-adjusting agent such as an acid to the composition. If an acid must be included in the composition to reduce the pH to the desired level, any acid may be used. Carboxylic acids are preferred because they are generally not fully dissociated in water and act in essence to buffer the composition at the desired pH. On the other hand, mineral acids (and some organic acids) are usually fully dissociated in water and will not provide the buffering effect. Accordingly, if acids are used that fully dissociate in water, buffering agents may be needed to maintain the pH at the desired level. The mineral acids that may be used include sulfuric and hydrochloric.

Acids such as acetic acid, propionic acid, and particularly hydroxycarboxylic acids such as lactic acid, glycolic acid, tartaric acid, malic acid, citric acid, and glucolic acid may be used, of which acetic and citric are preferred and citric is most preferred. Citric acid is believed to crystallize in the hair and thereby stiffen it.

The acids can be used in their acid form or in their salt form, e.g., their alkali metal salt form. Thus as used herein, the terms "an acid" or "an acid selected from the group consisting of carboxylic acids and mineral acids" should be understood to include their salts that when used in the composition of this invention will help provide the desired pH adjustment. When such an acid salt is used, additional acidic material may be required to provide a pH below about 4. The cost and availability of the various acids and acid salts will help determine which are used in the composition.

The amount of acid added to the composition will range from none (if the pH is already at the desired level) up to about 6.5% by weight of the composition, usually from about 0.001% to about 5% by weight of the composition, and more often from about 0.01% to about 3% by weight of the composition, and preferably from about 0.5% to about 2.5%.

Because it is desired that sufficient amounts of each of the "major ingredients" used in the composition of this invention (the polyvalent metal compounds, the sulfur-containing materials, and the acid) penetrate the hair fibers and that their presence ultimately results in the formation of sufficient disulfide bonds involving the keratin of the hair, it is important that the composition not contain excessive amounts of "hindering materials," by which is meant materials that because of their nature (e.g., hydrophobicity, film-forming tendency, adverse reactivity) prevent sufficient penetration of the major ingredients into the hair to achieve the benefits of this invention and/or prevent sufficient formation of disulfide bonds involving the keratin of the hair to achieve the benefits of this invention. Ideally the composition should contain no substance that forms a significant barrier to penetration into the hair fibers of the composition and its major ingredients (e.g., forms a significant barrier by coating the hair) and prevents sufficient formation of disulfide bonds involving the keratin of the hair.

"Hindering materials" can include polyhydroxyalcohols (e.g., glycerine, glycols), hydrophobic materials (e.g., mineral oils, silicones, fatty acids (for example, vegetable oils, safflower oil, oleic acid)), heavy metals that can break down peroxides, mineral thickeners (e.g., V-Gum, bentonite, and other clay and clay-like derivatives), some emulsifying agents (e.g., cetyl alcohols, stearyl alcohol), thickeners (e.g., cellulose gums in high concentrations; cellulose gums in low concentrations may be used unless they are in emulsions), mineral waxes (e.g., paraffins, ozocerites), and film-forming polymers (e.g., acrylics, styrene resins).

The total amount of hindering materials, if present, will usually be not greater than 10% by weight of the composition, more typically not greater than 5%, desirably not greater than 2%, more desirably not greater than 1%, most desirably not greater than 0.5%, preferably not greater than 0.25%, more preferably not greater than 0.1%, most preferably not greater than 0.01%, and sometimes not greater than 0.001% by weight of the composition. The amount and types of hindering materials that can be present without significantly adversely affecting the ability to achieve the benefits of the invention will depend on the particular composition.

If the composition does contain a substance that tends to coat the hair fibers, the substance desirably is non-ionic because ionic materials tends to further inhibit the penetration of the composition and major ingredients. Hair is hydrophobic and the composition of this invention is an aqueous composition (e.g., an aqueous solution). Therefore, if significant amounts of cationic materials are added to a composition of this invention, the cationic materials will tend to make it even more difficult for the composition of this invention to penetrate the hair fibers because the cationic materials will tend to repel the composition of this invention away from the hair fibers. For comparison, commercially available conditioner compositions often contain about 1.5 to 5% cationic materials, which are designed to stay on the outside of the hair fibers. Hair tends to "like" oils but oils also tend to inhibit the necessary penetration of the composition of this invention into the hair fibers. Other substances that are often found in commercially available hair treating compositions include silicones, thickeners (e.g., gums, polyglycols), and fragrances and may also pose a problem. Regardless of the nature and/or concentration of other ingredients in the composition of this invention, they should not prevent sufficient penetration of the composition into the hair fibers or prevent the advantages of this invention from being realized.

Generally, at least 10% of each of the at least one polyvalent metal compounds, the sulfur-containing materials, and the optional acid of the composition of this invention will be able to penetrate the hair within an hour. Desirably, at least 20% of each will be able to penetrate the hair within an hour. More desirably, at least 30% of each will be able to penetrate the hair within an hour. Preferably, at least 40% will be able to penetrate the hair within an hour. More preferably, at least 50% will be able to penetrate the hair within an hour. In some cases, significantly more that 50% of each of the at least one polyvalent metal compounds, the sulfur-containing materials, and the optional acid of the composition of this invention will be able to penetrate the hair within an hour. Generally speaking, the major ingredients of this composition will be carried into the hair fiber by and along with the aqueous carrier.

The composition of the invention can contain additives provided they do not significantly adversely affect the composition and its functioning (e.g., reduce penetration of the major ingredients into the hair fiber below the minimum required) so as to prevent the advantages of this invention from being achieved. The additives are not generally required to obtain the advantages of the invention but the efficacy, shelf-life, ease of application, and organoleptic properties of the invention can be improved by the presence of small amounts of the additives. Additives will usually be present in concentrations not exceeding about 25% (preferably not exceeding 15%) by weight of the composition although higher levels can be used in specific cases. The additives that can be used include fragrances, colorants, preservatives, viscosity control agents, penetration assistants (penetrants), water-miscible solvents, and wetting agents (surfactants) and are materials that are well-known in the art.

Fragrances and colorants may be added to improve the organoleptic and aesthetic properties of the composition for the consumer. The fragrances impart a pleasant odor or aroma to the product. The colorant can be included in the composition to provide a composition with a uniform attractive color and appearance.

When the pH of a composition of the present invention is towards the lower end of the pH range, a preservative usually will not be required because such pH values are biocidal or at least biostatic for organisms such as fungi, yeast, and bacteria. However, when the pH of the composition is towards the upper end of the pH range, it may be necessary to include preservatives in the composition so that it will have a useful (sufficiently long) shelf-life. Useful preservatives include methylparaben, ethylparaben, propylparaben, and butylated hydroxytoluene ("BHT").

The composition of the invention can contain viscosity control agents or thickeners to improve the ability of the composition to coat and cling to the hair fiber for a sufficient length of time (e.g., so that the major ingredients can penetrate the hair to the extent necessary and so that disulfide bonds can be formed inside as well as outside the hair fiber). As noted above, the viscosity control agents and thickeners should not prevent the required penetration of the major ingredients. The viscosity control agents and thickeners are generally polymeric materials and are well-known in the hair treatment art.

Penetrants can be included in the composition to increase the rate at which the composition penetrates the hair. The penetrants are generally water-miscible solvents that enhance the ability of the composition to penetrate the hair. Penetrants are well-known materials in the art.

Wetting agents (surfactants) may also be used in the composition of the invention. Wetting agents increase the rate at which the composition of the invention spreads over the hair surface. If the hair surface is wetted at a faster and more uniform rate, the probability for more even treatment is enhanced.

As discussed above, acid (including acid salt) may be required to adjust the pH to the desired range if the composition without the acid does not otherwise have the desired pH. However, it may also be advantageous to add non-acid materials to the composition to adjust the pH. Thus, it should be understood that the additives that can be employed in the composition of the present invention include such other non-acid pH-adjusting substances, e.g., alkali substances. Preferred alkaline substances to adjust the pH of the composition are the alkali metal hydroxides and ammonium hydroxide.

Buffering agents may be added to maintain or help maintain the pH of the composition at the desired level.

A mixture comprising the major ingredients and any additives can be prepared in a concentrated form and then diluted with water to form the composition of this invention for treating hair. Concentrates are useful because their use reduces packaging, handling, storage, and shipping costs. The composition of the invention may also be prepared as a two-package system with some of the ingredients of the composition in one package and the remaining ingredients in a second package. That two-package system may be useful in cases where the total composition in a single package does not have as long a shelf-life as the two separate partial compositions in two packages.

When the composition of the invention is applied to hair, the composition should be applied to cover substantially all of the hair fibers. The method of application of the composition of the invention is to some degree dependent on the arrangement of the hair at the time of application. Methods of applying treating liquids to hair are well-known in the art. The composition can be applied by blotting, misting, dipping, squeegeeing, or by using other methods known in the art. The method of application is not critical provided the composition is applied so as to coat substantially all of the hair fibers.

Processes

The composition of this invention may be used in a variety of processes, including rinse-free waving processes, coloring processes, combined rinse-free waving/coloring processes, conditioning, and pre-wrap processes. The composition of the present invention is particularly useful when used in conjunction with chemical hair treating processes, such as waving and coloring, to protect the hair from damage during a chemical treatment. As noted above, the term "waving" includes hair curling and hair straightening. Although the final results are different in hair waving and hair straightening processes, the process steps are similar and only the arrangement of the hair is different.

Rinse-free Waving

In the rinse-free waving process of this invention, the composition of the invention is applied to the hair after application of the waving (reducing) composition and before application of the neutralizer (oxidizing composition) without any intermediate rinsing step (i.e, a rinsing step between application of the waving solution and application of the neutralizer), thereby avoiding all of the disadvantages of that rinse step. The waved hair resulting from the process of this invention has stronger shape retention (whether a curled or straightened shape) and is shinier, stronger, softer, and more elastic than hair that is treated by the conventional permanent waving process. Furthermore, the hair can be shampooed immediately after the final rinse (the rinse to remove the neutralizer) without a substantial loss of curl.

A surprising advantage of this invention is that because of the use of the composition of this invention, the neutralizer may be left in contact with the hair for a longer period of time than that normally recommended by the manufacturer of the neutralizer. The longer neutralizer-hair contact time provides a more complete neutralization (oxidation or bonding) and without excessive damage to the hair. As a result of the additional neutralization time, the hair has springier and tighter curls than hair that has been treated by a conventional process (i.e., without the composition of this invention and typically with an intermediate rinse).

Obtaining hair that is softer than that obtained with a conventional treatment yet is stronger and has better shape retention is unexpected because increased strength and better shape retention in permanent waved hair are generally associated with a harder, stiffer hair fiber.

Broadly speaking, the rinse-free waving process of this invention comprises: optionally shampooing the hair; wrapping the hair on rods (if the hair is to be curled); applying a waving solution to hair according to the manufacturer's recommendations; allowing the waving solution to remain in contact with the hair; optionally removing excess waving composition without rinsing (e.g., by blotting) after the waving composition has relaxed the hair to the required degree; applying the composition of the invention to the hair; allowing that composition to remain in contact with the hair for at least 1 minute and preferably for 2 minutes or more after the application is complete; optionally removing excess composition without rinsing (e.g., by blotting); preferably gently heating the hair (at about 105° F., which is about 40° C.) to partial dryness (typically about 6 to 8 minutes); applying neutralizer according to the manufacturer's recommendations and permitting it to remain in contact with the hair for at least the recommended period (typically about 5 minutes) and preferably longer (at least 8 minutes); and removing the neutralizer, preferably by rinsing the hair while still on the rods. The hair can then be shampooed, conditioned, colored, highlighted, etc.

The permanent waving process of this invention usually starts with a shampoo to remove material (e.g., oils) from the hair that could interfere with the activity of the waving composition and/or the composition of this invention.

If the hair is to be curled, the hair is wound on rods to provide the mold for the curl size and shape. Waving composition (reducing solution) is then applied to the hair and permitted to remain in contact with the hair for a sufficient time to relax the hair, i.e., disrupt chemical bonds within the hair to permit the hair to relax (i.e., stop fighting against), the new arrangement or configuration. "Relaxation" of the hair also results in softening the feel of the hair as well as weakening it. If the hair is to be straightened and not curled, the hair is combed while in contact with the waving composition.

During contact with the waving composition, the hair can be heated to increase the rate at which the bonds are disrupted and the hair relaxed. The temperature and length of time during which the waving composition is contacted with the hair is dependent upon the components in the waving composition, and manufacturers' recommendations are followed. Contact time is usually from 3 to 30 minutes.

It is generally believed to be critical to achieving a successful permanent wave that as much of the waving composition as possible be removed from the hair, both that on the surface of the hair fibers and that which has penetrated into the hair fibers, after the hair has been softened and shaped to the required degree (i.e., after a sufficient number of chemical bonds have been cleaved). This belief arises from the fact that the waving composition is usually at a pH higher than that of the neutralizing composition (which is typically acidic) and that waving composition (a reducing agent) left on the hair can react with the neutralizing (oxidizing) agent and thereby reduce its effectiveness. Reduced effectiveness is detrimental because it reduces the number of disulfide bonds that can be formed to hold the hair in the desired new arrangement or configuration.

After the required amount of relaxation (i.e., breaking of the disulfide bonds in the hair) has occurred, the composition of the invention may be applied directly to the hair, i.e., without removing waving solution; however, it is preferred that the hair be blotted, preferably rod-by-rod, with an absorbent material (e.g., fabric or paper towels or tissues) to remove excess waving composition and to at least partially dry the hair before application of the composition of the invention. Blotting and partially drying the hair permit more rapid contact and more rapid penetration (the movement of the composition into the hair fibers is aided by wicking) and reaction of the composition of the invention with the hair.

The composition of the invention is preferably applied so that the composition contacts each hair fiber that has been treated with the waving composition to try to prevent subsequent direct contact between any residual waving composition and the neutralizing composition. Thorough wetting of the hair with the composition of the invention can be achieved by blotting, misting, or other techniques known for contacting hair with liquid composition, e.g., using a "snip top" applicator bottle. The quantity of composition applied to the hair is preferably the quantity required to bring the pH of the composition on the head to a pH of 7.0 or less and will typically be about the same amount as the amount of waving lotion applied.

The composition of the invention is permitted to remain in contact with the hair for at least 1 minute and preferably for 2 minutes or more after its application to the hair is completed. The hair is again blotted, preferably rod-by-rod, to remove excess composition. Preferably the hair is then gently heated at medium to high heat using a hooded dryer or other source of even heat for at least 5 minutes and preferably 6 to 8 minutes or more. The heating speeds the action of the composition of the invention to achieve chemical bonding within the hair fiber, namely, forming disulfide bonds involving the keratin of the hair.

The neutralizing composition (oxidizing agent) is then applied to the hair (while the hair is still on the rods if the hair is being curled, or while combing the hair if the hair is to be straightened) to rebond the chemical bonds that were broken during the waving treatment and thereby fix the hair in the new configuration or arrangement. In a conventional process (i.e., without the composition of this invention) the rebonding step typically requires from about 5 to about 8 minutes; however, a feature of this invention is that because of the application of the composition of this invention to the hair as part of this process, the contact time can be increased to at least 8 minutes and possibly up to 13 minutes. As noted above, the longer neutralizer-hair contact time provides a more complete neutralization (oxidation or bonding), without excessive damage to the hair, thereby giving the hair springier and tighter curls and providing other advantages. The longer contact time is possible with the process of the present invention because the composition of the invention protects the hair from the damaging effects of the neutralizer composition. The preferred neutralizer is hydrogen peroxide solution, preferably at a hydrogen peroxide concentration of 3% or more.

After sufficient neutralizer-hair contact time, the hair is rinsed, desirably while still on the rods (if the hair is being curled).

A preferred composition of the invention for the rinse-free process of this invention is described in Example 8, below, and may be described as follows. The aqueous composition contains 15% by weight Epsom salt ($MgSO_4 \cdot 7H_2O$), which is equivalent to roughly 7.5% by weight magnesium sulfate, 0.4% by weight CROTEIN WKP (hydrolyzed wool-based protein; 22% aqueous protein solution; average molecular weight of protein in solution is 600; cystine is 10.2% of protein), 0.3% by weight CROQUAT WKP (cocodimonium hydrolyzed animal keratin; 30% aqueous protein solution; average molecular weight of protein in solution is 1,000; cystine is 10.2% of protein), 0.2% fragrance (a mixture of two fragrance compositions marketed by Carruba, namely, Gardenia Fragrance No. A5462 and Citrus Fragrance No. A5224 in a 9/1 ratio), 2.19% anhydrous citric acid, and sufficient water to bring the total to 100%. The pH of the composition is 2.

Coloring

The process of this invention for coloring hair involves using the composition of the invention in connection with a coloring process and thereby improves the color depth (intensity) and color retention (color permanence) of the colored hair and also imparts softness, shine, luster, and elasticity to the colored hair. The coloring process of this invention may be carried out immediately after a waving process; however, the advantages of the coloring process of this invention are realized even when the coloring process is carried out several hours or days after a permanent waving treatment.

In the coloring process of this invention, the composition of the invention is contacted with the hair and remains in contact with the hair until the hair is either partially or fully dried, after which the hair is color treated according to the manufacturer's recommendations. (Fully dried is preferred; however, if the polyvalent metal concentration is sufficiently high, partial drying may be acceptable.) Desirably the composition of the invention is applied to the hair and remains in contact with the hair for at least 1 minute after the application has been completed. The hair is then contacted with heated air until the hair is dry, after which it is color treated.

The composition of this invention used in the coloring process of this invention preferably is an aqueous composition comprising 2–5% $MgSO_4 \cdot 7H_2O$, sufficient citric acid to give a pH of 3.5, 0.35% fragrance (a mixture of Gardenia Fragrance No. A5462 and Citrus Fragrance No. A5224 in a 9/1 ratio), and 1.5–3% of a mixture of CROTEIN WKP and CROQUAT WKP (in a weight ratio of 4 weight units of CROTEIN WKP to 3 weight units of CROQUAT WKP).

Combined Waving/Coloring

An unexpected process of the invention is a combined rinse-free/coloring process in which the color is applied to the hair after a permanent waving process without waiting the recommended time period between the permanent waving and the coloring process (that time period is typically a week or more). Thus, the hair can be permanently waved and colored in succession in just a single session, e.g., in just a single trip to the hair salon. As is well-known in the art, after a permanent waving treatment, the hair usually should not be further processed for at least 24 hours or else there may be significant loss of the wave imparted by the waving treatment. It is also generally believed not to be possible to color hair immediately after waving it without risking serious damage to the hair as well as skin and scalp irritation. In this combined process, it is believed that a less powerful developer can be used, which is advantageous because that reduces damage to the hair and irritation to the scalp.

According to the present invention, hair can be successfully colored immediately after a permanent waving treatment if the permanent wave is imparted by a process of the invention in which the composition of the invention is applied to the hair between application of the waving composition and application of the neutralizing composition. The advantages of this invention can also be achieved if after permanently waving the hair (either conventionally or according to the rinse-free waving process of this invention), the composition of the invention is applied to the hair after the waving process and before the color treatment. Thus, preferably if the rinse-free waving process of this invention is used (which employs the composition of this invention between reduction and oxidation) and the composition of this invention is used after the waving process is completed and before coloring, the hair will be contacted twice with compositions of this invention; however, the benefits of this invention can also be achieved if after a conventional waving process and before the coloring process the composition of this invention is applied to the hair.

Thus, in the preferred combined permanent waving/coloring process of the invention, the permanent wave is imparted to the hair according to the rinse-free waving process of the invention (with application of a composition of this invention to the hair between application of the waving and neutralizer solutions and without an intermediate rinse), the neutralizer is rinsed from the hair, the hair is thoroughly towel-blotted, and a composition of the invention is again applied to thoroughly wet the hair. The hair preferably is combed through, sectioned, and dried. Drying is preferably accomplished by passing a heated air stream over the hair, for example, by means of a hair dryer or a hooded dryer. The heated air stream hastens drying and the slightly elevated temperature promotes penetration and the desired reaction in the hair. After drying, the hair is colored according to manufacturer's recommendations. Except for the waving process itself the steps are the same in the less preferred combined waving/coloring process (in which a conventional waving process is used) as in the more preferred combined waving/coloring process (in which the rinse-free waving process of this invention is used).

As compared to hair waved by a conventional process and then colored more than a week later without any use of the composition of the invention, hair colored immediately after a permanent waving treatment according to the combined waving/coloring process of this invention has a deeper color, is shinier, softer, and holds a curl that is approximately equivalent to the curl in the conventionally waved and colored hair.

If compositions of this invention are to be used twice in the combined waving/coloring process of this invention (the first during a rinse-free wave and the second following the wave but before the coloring), the first composition of this invention used (in the rinse-free wave part of the combined process) preferably has the same composition as the preferred composition used in the rinse-free process set forth above (namely, 15% by weight $MgSO_4 \cdot 7H_2O$, 0.4% by weight CROTEIN WKP, 0.3% by weight CROQUAT WKP, 0.2% fragrance (a mixture of Gardenia Fragrance No. A5462 and Citrus Fragrance No. A5224 in a 9/1 ratio), 2.19% anhydrous citric acid, and sufficient water to bring the total to 100%, with a pH of 2) and the second composition of this invention used (after waving but before coloring) preferably has the same composition as the preferred composition used in the coloring process set forth above (namely, 2–5% $MgSO_4 \cdot 7H_2O$, sufficient citric acid to give a pH of 3.5, 0.35% fragrance (a mixture of Gardenia Fragrance No. A5462 and Citrus Fragrance No. A5224 in a 9/1 ratio), and 1.5–3% of a mixture of CROTEIN WKP and CROQUAT WKP in a weight ratio of 4 weight units of CROTEIN WKP to 3 weight units of CROQUAT WKP). If the composition of this invention is to be used just once in the combined waving/coloring process of this invention (following a conventional wave but before the coloring), the composition of this invention used preferably has the same composition as the preferred composition used in the coloring process set forth above (namely, 2–5% $MgSO_4 \cdot 7H_2O$, sufficient citric acid to give a pH of 3.5, 0.35% fragrance (a mixture of Gardenia Fragrance No. A5462 and Citrus Fragrance No. A5224 in a 9/1 ratio), and 1.5–3% of a mixture of CROTEIN WKP and CROQUAT WKP in a weight ratio of 4 weight units of CROTEIN WKP to 3 weight units of CROQUAT WKP).

Conditioning

According to the conditioning process of this invention, application of the composition of the invention to hair imparts improved properties to chemically damaged hair. The composition can be applied to shampooed damp hair, encased with a plastic cap, and placed under a hooded dryer on medium to high heat (about 105° F., which is about 40° C.) for 5 to 15 minutes, after which the hair is rinsed. The hair is shinier, softer, stronger, and more elastic with reduced frizzing. The composition of the invention is particularly useful for repairing some of the damage caused by various chemical hair treatments, such as permanent waving, coloring, and bleaching. The effect of treatment with the composition of the invention lasts through several shampoos.

The composition of this invention used in the conditioning process of this invention preferably has about the same composition as the preferred composition of this invention used in the color process of this invention (namely, 2–5% $MgSO_4 \cdot 7H_2O$, 0.35% fragrance (a mixture of Gardenia Fragrance No. A5462 and Citrus Fragrance No. A5224 in a 9/1 ratio), and 1.5–3% of a mixture of CROTEIN WKP and CROQUAT WKP in a weight ratio of 4 weight units of CROTEIN WKP to 3 weight units of CROQUAT WKP), except for adjusting the pH to 3.5 to 5.5 with citric acid, if necessary).

Pre-Wrap

The invention also concerns a process known as a protein treatment or "pre-wrap," which is used on previously processed hair just prior to applying the reducing solution in a permanent waving process. The composition can be applied on shampooed towel-blotted hair. Enough of the composition of the invention is applied so that the hair is wet but not dripping. The hair is combed to distribute the composition throughout the hair and allowed to remain on the hair for at least 1 minute prior to beginning the permanent wave wrap.

The effect of this pre-wrap treatment with the composition of the invention is to reduce the porosity of the hair and protect the hair from many of the damaging effects of the permanent waving reducing solution and achieve stronger, springier, more helically shaped curls in processed hair.

The composition of this invention used in the pre-wrap process of this invention preferably comprises 1% $MgSO_4 \cdot 7H_2O$, 0.35% fragrance (a mixture of Gardenia Fragrance No. A5462 and Citrus Fragrance No. A5224 in a 9/1 ratio), 1.5% of a mixture of CROTEIN WKP and CROQUAT WKP in a weight ratio of 4 weight units of CROTEIN WKP to 3 weight units of CROQUAT WKP, and sufficient citric acid and/or pH-adjusting additives to give a pH of 4.5 to 5.5.

Examples

The following examples are provided for illustrative purposes and should not be used to unduly limit the scope of the invention.

Examples 1–15 used 2.0 grams of intact (i.e., Virgin) Remis Italian, Medium Brown Hair obtained from R. Parino Hair Goods. The hair fibers in the tresses measured 8 inches (20.3 centimeters) in length and were bound at the root end with epoxy. Tresses were wet with water and wound for 3–4 full revolutions on a standard white rod (about 1.3 centimeters in diameter at the two large ends and 0.65 centimeters at the center) using a 150-gram weight as a counterbalancing force. Wound hair was then saturated with 3.0 milliliters waving lotion. The waving lotion used is identified in each Table. Tresses were covered with a plastic film and maintained at approximately 105° F. (about 40° C.) for the processing time indicated in each table.

After the processing period, all tresses were blotted with an absorbent paper towel and 3.0 milliliters of the respective aqueous formulation identified in the Tables was applied to the tress; no tress was rinsed with water, as would be the case with a conventional perming (waving) process. In all Examples, the formulations contained 15% by weight $MgSO_4 \cdot 7H_2O$ and 0.2% by weight fragrance (a mixture of Gardenia Fragrance No. A5462 and Citrus Fragrance No. A5224 in a 9/1 ratio). All formulations contained the concentration of commercially available aqueous protein solution shown in the Tables. Those protein solutions vary as to the source of their protein, their concentration of protein in the protein solution, and their concentration of cystine in the protein. All formulations were adjusted to a pH of 2.0 by addition of sufficient citric acid.

The formulation was applied and allowed to contact the hair for 2 minutes, after which each tress was blotted while still on the rod and dried using a blow dryer located 10 inches from the tress at medium heat for about 1 minute. After the hair was dry to the touch, 3 milliliters of neutralizer was applied. After processing (contacting the hair with the neutralizer) for 8 minutes, the hair was rinsed for about 30 seconds on the rod and 30 seconds off the rod (the total rinsing time of 1 minute is the time typically used for rinsing 1 quadrant of the head). The neutralizer used in Examples 1–7 was a 3.5% hydrogen peroxide solution; the neutralizer used in Examples 8–15 was the manufacturer's hydrogen peroxide solution.

The controls (to which the processed hair of the Examples is compared) for Tables 1 and 3 (Example 1–5 and 8–15) were conventionally permed tresses of the same hair prepared using the waving lotion identified in each Table. The control for Table 2 was Example 5. The control for Table 1 (Examples 1–5) used a 3.5% hydrogen peroxide neutralizing solution. The control for Table 3 (Examples 8–15) used the manufacturer's hydrogen peroxide neutralizing solution. The conventionally permed tresses (the controls for Examples 1–5 and 8–15) received the same treatment as the tresses of the Examples except that the conventionally permed tresses were rinsed for about 1 minute in warm water prior to blotting and drying in advance of neutralization, i.e, they received the intermediate rinse between application of the reducing and neutralization solutions, which intermediate rinse the tresses of the Examples did not receive.

Tresses were rated on strength of curl and odor retention. The strength-of-curl evaluation compared the curl strength of the Example tresses to the curl strength of the respective Control. Curl strength was evaluated by a trained cosmetologist based on the length of the tress subsequent to the perm and the resulting "S" pattern. The curl evaluation rating scale used is as follows:

"–3" means unacceptable curl strength
"–2" means curl strength much weaker than Control
"–1" means curl strength slightly weaker than Control
"0" means curl strength approximately equal to Control
"+1" means curl strength slightly stronger than Control
"+2" means curl strength much stronger than Control
"+3" means curl strength is exceptional and significantly stronger than Control.

An "S" evaluation indicates that when wet, a sulfur-like odor was detected, which might indicate excessive thioglycolic residue in the hair; an "S+" indicates that the detectable odor was significant when the tress was wet. If no "S" is indicated, there was no detectable odor.

Except for the Hask Placenta, the commercially available protein solutions used are available from Croda Inc. and have the following characteristics:

CROTEIN WKP—hydrolyzed wool-based keratin protein; 22% aqueous protein solution; average molecular weight of protein in solution is 600; cystine is 10.2% of protein CROQUAT WKP—cocodimonium (cationic) hydrolyzed wool-based keratin; 30% aqueous protein solution; average molecular weight of protein in solution is 1,000; cystine is 10.2% of protein CROSILKQUAT—cationic silk amino acids; 30% aqueous solution; average molecular weight of protein in solution is 320; cystine is 0.1% of protein CROQUAT M—hydrolyzed collagen protein; 40% aqueous protein solution; average molecular weight of protein in solution is 2,500; cystine is 0.1% of protein HYDROSOY 2000/SF—soy protein; 20% aqueous protein solution; average molecular weight of protein in solution is 4,000; cystine is 1.2% of protein HYDROTRITICUM—hydrolyzed whole wheat protein; 20% aqueous protein solution; average molecular weight of protein in solution is 3,000; cystine is 1.8% of protein CROTEIN SPA 55—hydrolyzed collagen protein; 55% aqueous protein solution; average molecular weight is 4,000; cystine is 0.9% of protein Hask Placenta—referenced in U.S. Pat. No. 4,906,461

In the Tables, the following terms are used:

"Protein Commercial Solution"—the name of the solution under which Croda Inc. sells the composition containing the proteinaceous material.

"Pr. Avg. MW" or "Protein Average Molecular Weight"—the number average molecular weight of the proteinaceous material in the commercial composition sold by Croda Inc.

"Protein Comp. Conc. In Form."—the concentration (weight %) in the formulation applied to the hair of the Croda Inc. commercial composition containing the proteinaceous material.

"Protein Conc. In Form."—the concentration (weight %) of total protein in the formulation applied to the hair; calculated by multiplying (i) the concentration of Croda Inc. commercial composition in the formulation by (ii) the concentration of proteinaceous material in the Croda Inc. commercial composition (e.g., for Example 1: 0.01×0.22, which equals 0.0022 or 0.22%; for Example 2: 0.01×0.30, which equals 0.0030 or 0.30%)

"Cystine Conc. In Protein"—the concentration of cystine in the protein of the commercial composition "Cystine In Form."—the cystine content in parts per million by weight of the formulation applied to the hair; calculated by multiplying (i) the concentration of Croda Inc. commercial composition in the formulation by (ii) the concentration of proteinaceous material in the Croda Inc. commercial composition by (iii) the cystine concentration of the proteinaceous material (e.g., for Example 1: 0.01×0.22× 0.102, which equals 0.000224 or 224 ppm; for Example 2: 0.01×0.30×0.102, which equals 0.000306 or 306 ppm); the sulfur concentration of cystine is 26.7%, thus the sulfur content of the formulation may be calculated by multiplying the formulation's cystine content in ppm by 0.267.

"Post-Perm Eval'n"—the evaluation of the hair made after the permanent waving process has been completed.

"Eval'n After 1st Shampoo"—the evaluation of the hair made after the permanent waving process has been completed and the hair has been shampooed once.

"Eval'n After 2nd Shampoo"—the evaluation of the hair made after the permanent waving process has been completed and the hair has been shampooed twice.

"Eval'n After 3rd Shampoo"—the evaluation of the hair made after the permanent waving process has been completed and the hair has been shampooed three times.

TABLE 1

Performance of Different Proteins in Rinse-Free Formulation

| Example | Protein Commercial Solution | Protein Comp. Conc. In Form. | Protein Conc. In Form. | Cystine Conc. In Protein | Cystine In Form. (PPM) | Post-Perm Eval'n | Eval'n After 1st Shampoo | Eval'n After 2nd Shampoo | Eval'n After 3rd Shampoo |
|---|---|---|---|---|---|---|---|---|---|
| 1 | CROTEIN WKP (Pr. Avg. MW = 600) | 1.0% | 0.22% | 10.2% | 224 | 0 | 0 | 0 | −1 |
| 2 | CROQUAT WKP (Pr. Avg. MW = 1,000) | 1.0% | 0.30% | 10.2% | 306 | 0,S | 0 | 0 | −1 |
| 3 | CROSILKQUAT (Pr. Avg. MW = 320) | 1.0% | 0.30% | 0.1% | 3 | −1 | −1 | −1 | −2 |
| 4 | CROQUAT M (Pr. Avg. MW = 2,500) | 1.0% | 0.40% | 0.1% | 4 | −2,S+ | −2,S+ | −3,S+ | −3,S+ |
| 5 | CROQUAT WKP (Pr. Avg. MW = 1,000) CROTEIN WKP (Pr. Avg. MW = 600) | 0.5% 0.5% | 0.26% (total) | 10.2% 10.2% | 265 | +1 | +1 | +1 | +1 |

Waving lotion used was Tressa's VERSATAGE, which is an alkaline thioglycolate wave having a pH of 9.2. The neutralizer was a lab-prepared 3.5% hydrogen peroxide solution. Processing time was 28 minutes. The "Control" for all examples was a conventionally waved tress using the VERSATAGE waving lotion and the 3.5% hydrogen peroxide solution.

TABLE 2

Performance of Different Proteins in Rinse-Free Formulation

| Example | Protein Commercial Solution | Protein Average Molecular Weight | Protein Comp. Conc. In Form. | Cystine Conc. In Protein | Cystine In Form. (PPM) | Post-Perm Eval'n | Eval'n After 1st Shampoo |
|---|---|---|---|---|---|---|---|
| 6 | HYDROSOY 2000/SF | 4,000 | 1% | 1.2% | 20 | +2 | −2 |
| 7 | HYDROTRITICUM | 3,000 | 1% | 1.8% | 36 | −1,S | −3 |

Waving lotion used was Tressa's VERSATAGE, which is an alkaline thioglycolate wave having a pH of 9.2. The neutralizer was a lab-prepared 3.5% hydrogen peroxide solution. Processing time was 28 minutes. The "Control" for both examples was Example 5.

TABLE 3

Performance of Different Proteins and Protein Levels in Rinse-Free Formulation

| Example | Protein Commercial Solution | Protein Average Molecular Weight | Protein Comp. Conc. In Form. | Cystine Conc. In Protein | Cystine In Form. (PPM) | Post-Perm Eval'n | Eval'n After 1st Shampoo |
|---|---|---|---|---|---|---|---|
| 8 | CROQUAT WKP | 1,000 | 0.3% | 10.2% | 182 | +1 | +1 |
|   | CROTEIN WKP | 600 | 0.4% | 10.2% |   |   |   |
| 9 | HYDROSOY 2000/SF | 4,000 | 0.14% | 1.2% | 3 | 0 | −3 |
| 10 | HYDROSOY 2000/SF | 4,000 | 0.70% | 1.2% | 14 | −1 | −3 |
| 11 | CROSILKQUAT | 320 | 0.14% | 0.1% | <1 | 0 | −3 |
| 12 | CROSILKQUAT | 320 | 0.70% | 0.1% | 2 | 0 | −3 |
| 13 | CROTEIN SPA 55 | 4,000 | 0.14% | 0.9% | 7 | −1 | −3 |
| 14 | CROTEIN SPA 55 | 4,000 | 0.70% | 0.9% | 35 | −2 | −3 |
| 15 | Hask Placenta | not available | trace | trace | <1 | −1 | −3 |

Waving lotion used was Zotos BAIN D TERRE NATURAGE, the pH of which is 9.0. The neutralizer concentration was the BAIN DE TERRE NATURAGE neutralizer. Processing time was 30 minutes. The "Control" was a conventionally waved tress using the BAIN DE TERRE NATURAGE waving lotion and neutralizer. Odor was not rated.

Examples 16–19 used the same processing technique as Examples 1–15. Examples 16–18 used the same kind of hair at the same length and weight as Examples 1–15. Example 19 used approximately 5 inches of light brown hair weighing 1 gram, which was obtained from a post-pubescent teenager. In Examples 16–19, the formulations contained 0.2% fragrance, sufficient anhydrous citric acid to adjust the composition to a pH of 2.0, and $MgSO_4 \cdot 7H_2O$ levels and protein levels shown in Table 4.

A conventionally permed tress for use as the Control for Example 16–18 was prepared using the waving lotion and neutralizer identified in Table 4. The conventionally permed tress received the same treatment as the other Control tresses for Tables 1 and 3. The Control for Example 19 was the same hair and wave (Tressa's VERSATAGE) used in Example 19 but using the rinse-free process of this invention with the preferred rinse-free composition of this invention.

Tresses in Examples 16–19 were rated on strength of curl, softness of hair, and color retention. The strength-of-curl evaluation used the scale described above and compared the curl strength of the Example tresses to the curl strength of the respective Control tress. A notation of "H" indicates that the hair had a hard feel; an "L" indicates that the hair appeared visibly lighter.

As above, an "S" evaluation indicates that when wet, a sulfur-like odor was detected, which might indicate excessive thioglycolic residue in the hair.

TABLE 4

Performance of Different Magnesium and Protein Levels in Rinse-Free Formulation

| Examples | $MgSO_4 \cdot 7H_2O$ Content | Protein Comp. Conc. In Form. | Post-Perm Eval'n | Eval'n After 1st Shampoo |
|---|---|---|---|---|
| 16 | 3% | 0.0% | −1 | −1 |
| 17 | 25% | 0.0% | 0,H,S | 0,H |
| 18 | 0% | 3.0% (1.5% CROTEIN WKP; 1.5% CROQUAT WKP) | −3,S | −1 |
| 19 | 15% | 0.0% | +1,L,H | +1,L,H |

Perm used a Tressa's VERSATAGE having a 9.2 pH. The neutralizer for Examples 16, 17, and 19 was a lab-prepared 3.5% hydrogen peroxide solution; the neutralizer for Example 18 was a lab-prepared 4.0% hydrogen peroxide solution. The "Control" for Examples 16, 17, and 18 was a conventionally waved tress using the VERSATAGE waving lotion and the 3.5% hydrogen peroxide neutralizer; the "Control" for Example 19 was a tress permed with the rinse-free process of this invention using the VERSATAGE waving lotion and the 3.5% hydrogen peroxide neutralizer.

These Examples demonstrate the benefits of this invention. Example 8, which is within the scope of the invention, shows that the rinse-free waving process of this invention (which uses the composition of this invention and omits the rinse between application of the waving solution and neutralizer) provides a permanent wave superior to the wave provided by a conventional process: the wave was superior both after completion of the waving process and after the hair had been shampooed once.

The Examples also show that a cationic and neutral protein in combination may in some cases provide superior performance to use of either protein alone (compare Example 5, which uses the combination, with Examples 1 and 2).

The Examples also show that substances that do not contain sufficient sulfur-containing material that can form disulfide bonds involving the keratin of the hair (e.g., sufficient cystine) do not provide the benefits of this invention. For example, compare Examples 3 and 4 to Example 5. The formulation of Example 3 contains about 3 ppm cystine and a total proteinaceous material concentration of 0.3%; and the concentration of sulfur in the sulfur-containing material that can form disulfide bonds involving the keratin of the hair is less than about 0.03% (which is calculated by multiplying the cystine concentration of the proteinaceous material, 0.1%, by the sulfur concentration in cystine, 26.7%). The formulation of Example 4 contains about 4 ppm cystine and a total proteinaceous material concentration of 0.4%; and the concentration of sulfur in the sulfur-containing material that can form disulfide bonds involving the keratin of the hair is about 0.03% (which is calculated by multiplying the cystine concentration of the proteinaceous material, 0.1%, by the sulfur concentration in cystine, 26.7%). The formulation of Example 5 contains less total proteinaceous material than the formulation of either Example 3 or 4 (it contains 0.26% total proteinaceous material, which is calculated as follows: 0.5%×22% for CROTEIN WKP plus 0.5%×30% for CROQUAT WKP) but it contains substantially more cystine (about 265 ppm) than the formulation of either Example 3 or 4 (265 ppm compared to 3 and 4 ppm), and the concentration of sulfur in the sulfur-containing material that can form disulfide bonds involving the keratin of the hair is about 2.7% (which is calculated by multiplying the cystine concentration of the proteinaceous material, 10.2%, by the sulfur concentration in cystine, 26.7%).

The Examples also show that proteinaceous material outside the scope of the invention may possibly provide better properties after perming but those properties are not long-lasting, e.g., they do not stand up to shampooing. See Example 6, the Control for which was Example 5.

The Examples also show that magnesium sulfate yields a strong curl but contributes hardness (see Examples 17 and 19) and can in some hair result in a visible lightening or frizzing of the hair (see Example 19, the Control for which employed a composition of this invention). Protein in the composition helps impart a soft feel to the hair; however, protein alone cannot deliver a strong curl (see Example 18). It may be possible in some cases to use the sulfur-containing material without the polyvalent metal in a rinse-free waving process if the neutralizer (e.g., hydrogen peroxide) is "strong enough," that is, is more powerful or concentrated than is typically the case. (In neutralizer solution, hydrogen peroxide can be found in concentrations of 2–3.5%.)

As will be understood by one skilled in the art, many variations and modifications may be made and the claims are intended to cover all variations and modifications falling within the true spirit and scope of the invention.

We claim:

1. An aqueous composition useful for treating hair, which can be used to prevent or repair damage to the hair caused by hair treating processes or by environmental factors and which can be applied to the hair in a process involving waving after waving solution has been applied to the hair and before oxidizing agent has been applied to the hair to improve curl retention, color receptivity, color stability, color retention, shine, and/or strength, the composition comprising the ingredients:
   (a) at least 1% by weight total of one or more polyvalent metal compounds selected from the group consisting of alkaline earth metal compounds, zinc compounds, and aluminum compounds;
   (b) at least 0.05% by weight of cystine-containing proteinaceous material that has an average molecular weight of 10,000 or less, that can form disulfide bonds involving the keratin of the hair, and whose cystine content is at least about 3.5% by weight, the concentration of the cystine-containing proteinaceous material in the aqueous composition and its cystine content being such that the cystine content of the aqueous composition is at least 0.005% by weight; and
   (c) optionally, an acid;
   the pH of the composition being less than 10.

2. The composition of claim 1 wherein at least one of the one or more polyvalent metal compounds is selected from the group consisting of magnesium and calcium compounds.

3. The composition of claim 1 wherein at least one of the one or more polyvalent metal compounds is selected from the group consisting of magnesium sulfate, calcium chloride, calcium acetate, magnesium chloride, zinc chloride, zinc sulfate, and aluminum sulfate.

4. The composition of claim 1 wherein the one or more polyvalent metal compounds are present in a total amount of at least 2% by weight.

5. The composition of claim 1 wherein the one or more polyvalent metal compounds are present in a total amount of from 3 to 20% by weight.

6. The composition of claim 1 wherein the one or more polyvalent metal compounds are present in a total amount of from 4 to 15% by weight.

7. The composition of claim 1 wherein the one or more polyvalent metal compounds are present in a total amount of from 5 to 12.5% by weight.

8. The composition of claim 1 wherein the one or more polyvalent metal compounds are present in a total amount of from 6 to 9% by weight.

9. The composition of claim 1 wherein the concentration of the proteinaceous material in the aqueous composition and its cystine content are such that the cystine content of the aqueous composition is at least 0.010% by weight.

10. The composition of claim 1 wherein the proteinaceous material has an average molecular weight of 2,000 or less.

11. The composition of claim 1 wherein the proteinaceous material contains at least about 6% cystine.

12. The composition of claim 1 wherein the proteinaceous material contains at least about 8% cystine.

13. The composition of claim 1 wherein the proteinaceous material contains at least about 10% cystine.

14. The composition of claim 1 wherein an acid is used and it is selected from the group consisting of carboxylic acids and mineral acids.

15. The composition of claim 1 wherein the acid is used and it is selected from the group consisting of hydroxycarboxylic acids and mineral acids.

16. The composition of claim 1 wherein the pH is 6.5 or less.

17. The composition of claim 1 wherein the pH is 6.5 or less, at least one of the one or more polyvalent metal compounds is magnesium sulfate, the acid is citric acid and is present in an amount of from 0.01 to 3% by weight, and the proteinaceous material contains at least 6% cystine and is present in an amount of from 0.1 to 4% by weight.

18. The composition of claim 17 wherein the proteinaceous material comprises non-ionic and cationic proteinaceous materials in a weight ratio of from 4/1 to 1/4.

19. The composition of claim 17 wherein the proteinaceous material contains at least 8% cystine.

20. The composition of claim 19 wherein the proteinaceous material comprises non-ionic and cationic proteinaceous materials in a weight ratio of from 4/1 to 1/4.

21. The composition of claim 10 wherein at least one of the one or more polyvalent metal compounds is selected from the group consisting of magnesium and calcium compounds.

22. The composition of claim 10 wherein at least one of the one or more polyvalent metal compounds is selected from the group consisting of magnesium sulfate, calcium chloride, calcium acetate, magnesium chloride, zinc chloride, zinc sulfate, and aluminum sulfate.

23. The composition of claim 10 wherein the one or more polyvalent metal compounds are present in a total amount of at least 2% by weight.

24. The composition of claim 10 wherein the one or more polyvalent metal compounds are present in a total amount of from 3 to 20% by weight.

25. The composition of claim 10 wherein the one or more polyvalent metal compounds are present in a total amount of from 4 to 15% by weight.

26. The composition of claim 10 wherein the one or more polyvalent metal compounds are present in a total amount of from 5 to 12.5% by weight.

27. The composition of claim 10 wherein the one or more polyvalent metal compounds are present in a total amount of from 6 to 9% by weight.

28. The composition of claim 10 wherein the concentration of the proteinaceous material in the aqueous composition and its cystine content are such that the cystine content of the aqueous composition is at least 0.010% by weight.

29. The composition of claim 10 wherein the proteinaceous material contains at least about 6% cystine.

30. The composition of claim 10, wherein the proteinaceous material contains at least about 8% cystine.

31. The composition of claim 10 wherein the proteinaceous material contains at least about 10% cystine.

32. The composition of claim 1 wherein the acid is present and is a hydroxycarboxylic acid.

33. The composition of claim 1 wherein an acid is used and it is selected from the group consisting of citric, acetic, hydrochloric, and sulfuric acids.

34. The composition of claim 1 where the pH is from 3.5 to 6.5.

35. The composition of claim 1 where the pH is from 2.0 to 3.5.

36. The composition of claim 10, wherein the pH is 6.5 or less, at least one of the one or more polyvalent metal compounds is magnesium sulfate, the acid is citric acid and is present in an amount of from 0.01 to 3% by weight, and the proteinaceous material contains at least 6% cystine and is present in an amount of from 0.1 to 4% by weight.

37. The composition of claim 36 wherein the proteinaceous material comprises non-ionic and cationic proteinaceous materials in a weight ratio of from 4/1 to 1/4.

38. The composition of claim 36 wherein the proteinaceous material contains at least 8% cystine.

39. The composition of claim 38 wherein the proteinaceous material comprises non-ionic and cationic proteinaceous materials in a weight ratio of from 4/1 to 1/4.

40. An aqueous composition useful for treating hair, which can be used to prevent or repair damage to the hair caused by hair treating processes or by environmental factors and which can be applied to the hair in a process involving waving after waving solution has been applied to the hair and before oxidizing agent has been applied to the hair to improve curl retention, color receptivity, color stability, color retention, shine, and/or strength, the composition comprising the ingredients:

(a) at least 2% by weight total of one or more polyvalent metal compounds selected from the group consisting of alkaline earth metal compounds, zinc compounds, and aluminum compounds;

(b) at least 0.05% by weight of cystine-containing proteinaceous material that has an average molecular weight of 10,000 or less, that can form disulfide bonds involving the keratin of the hair, and whose cystine content is at least about 3.5% by weight, the concentration of the cystine-containing proteinaceous material in the aqueous composition and its cystine content being such that the cystine content of the aqueous composition is at least 0.005% by weight; and (c) an acid selected from the group consisting of carboxylic acids and mineral acids;

the pH of the composition being less than 10.

41. The composition of claim 40 wherein the one or more polyvalent metal compounds are present in a total amount of from 3 to 20% by weight.

42. The composition of claim 40 wherein the one or more polyvalent metal compounds are present in a total amount of from 4 to 15% by weight.

43. The composition of claim 40 wherein the one or more polyvalent metal compounds are present in a total amount of from 5 to 12.5% by weight.

44. The composition of claim 40 wherein the one or more polyvalent metal compounds are present in an amount of from 6 to 9% by weight.

45. The composition of claim 40 wherein the proteinaceous material contains at least about 6% cystine.

46. The composition of claim 40 wherein the proteinaceous material contains at least about 8% cystine.

47. The composition of claim 40 wherein the proteinaceous material contains at least about 10% cystine.

48. The composition of claim 40 wherein the acid is selected from the group consisting of hydroxycarboxylic acids and mineral acids.

49. The composition of claim 40 wherein the pH is 6.5 or less.

50. The composition of claim 40 wherein the pH is 6.5 or less, at least one of the one or more polyvalent metal compounds is magnesium sulfate, the acid is citric acid and is present in an amount of from 0.01 to 3% by weight, and the proteinaceous material contains at least 6% cystine and is present in an amount of from 0.1 to 4% by weight.

51. The composition of claim 50 wherein the proteinaceous material comprises non-ionic and cationic proteinaceous materials in a weight ratio of from 4/1 to 1/4.

52. The composition of claim 50 wherein the proteinaceous material contains at least 8% cystine.

53. The composition of claim 52 wherein the proteinaceous material comprises non-ionic and cationic proteinaceous materials in a weight ratio of from 4/1 to 1/4.

54. An aqueous composition useful for treating hair, which can be used to prevent or repair damage to the hair caused by hair treating processes or by environmental factors and which can be applied to the hair in a process involving waving after waving solution has been applied to the hair and before oxidizing agent has been applied to the hair to improve curl retention, color receptivity, color stability, color retention, shine, and/or strength, the composition comprising the ingredients:

(a) at least 1% by weight total of one or more polyvalent metal compounds selected from the group consisting of alkaline earth metal compounds, zinc compounds, and aluminum compounds;

(b) at least 0.05% by weight of cystine-containing proteinaceous material that has an average molecular weight of 10,000 or less, that can form disulfide bonds involving the keratin of the hair, and that comprises non-ionic hydrolyzed animal keratin protein and cationic hydrolyzed animal keratin protein, the concentration of the cystine-containing proteinaceous material as a whole in the aqueous composition and its cystine content being such that the cystine content of the aqueous composition is at least 0.005% by weight; and (c) optionally, 0.001 to 5% by weight of an acid selected from the group consisting of carboxylic acids and mineral acids;

the pH of the composition being less than 10.

55. The composition of claim 54 wherein at least one of the one or more polyvalent metal compounds is magnesium sulfate and the acid is present and is citric acid.

56. The composition of claim 54 wherein the cystine-containing proteinaceous material as a whole contains at least about 3.5% cystine.

57. The composition of claim 54 wherein the pH is 6.5 or less, at least one of the one or more polyvalent metal compounds is magnesium sulfate, the acid is citric acid and is present in an amount of from 0.01 to 3% by weight, and the cystine-containing proteinaceous material as a whole contains at least about 3.5% cystine and is present in an amount of from 0.1 to 4% by weight.

58. The composition of claim 57 wherein the non-ionic and cationic hydrolyzed animal keratin proteins are present in a weight ratio of from 4/1 to 1/4.

59. The composition of claim 54 wherein the cystine-containing proteinaceous material as a whole contains at least about 6% cystine.

60. The composition of claim 59 wherein the non-ionic and cationic hydrolyzed animal keratin proteins are present in a weight ratio of from 4/1 to 1/4.

61. The composition of claim 54 wherein the concentration of the cystine-containing proteinaceous material as a whole in the aqueous composition and its cystine content are such that the cystine content of the aqueous composition is at least 0.010% by weight.

62. The composition of claim 54 wherein the concentration of the cystine-containing proteinaceous material as a whole in the aqueous composition and its cystine content are such that the cystine content of the aqueous composition is at least 0.015% by weight.

63. The composition of claim 54 wherein the cystine-containing proteinaceous material as a whole has an average molecular weight of 2,000 or less.

64. The composition of claim 56 wherein the concentration of the cystine-containing proteinaceous material as a whole in the aqueous composition and its cystine content are such that the cystine content of the aqueous composition is at least 0.010% by weight.

65. The composition of claim 56 wherein the concentration of the cystine-containing proteinaceous material as a whole in the aqueous composition and its cystine content are such that the cystine content of the aqueous composition is at least 0.015% by weight.

66. The composition of claim 56 wherein the cystine-containing proteinaceous material as a whole has an average molecular weight of 2,000 or less.

67. The composition of claim 66 wherein the non-ionic and cationic hydrolyzed animal keratin proteins are present in a weight ratio of from 4/1 to 1/4.

68. The composition of claim 59 wherein the cystine-containing proteinaceous material as a whole has an average molecular weight of 2,000 or less.

69. The composition of claim 40 wherein the concentration of the proteinaceous material in the aqueous composition and its cystine content are such that the cystine content of the aqueous composition is at least 0.010% by weight.

* * * * *